United States Patent [19]

Renga

[11] 4,336,195
[45] Jun. 22, 1982

[54] PREPARATION OF CYCLIC ETHERS
[75] Inventor: James M. Renga, Midland, Mich.
[73] Assignee: The Dow Chemical Company, Midland, Mich.
[21] Appl. No.: 230,245
[22] Filed: Feb. 2, 1981
[51] Int. Cl.³ .................. C07D 319/10; C07D 307/00; C07D 307/77; C07D 309/00
[52] U.S. Cl. .................................. 549/462; 549/369; 549/377; 549/356; 549/508
[58] Field of Search ............. 260/340.6, 340.9, 346.11, 260/346.22, 345.1

[56] References Cited

U.S. PATENT DOCUMENTS

| | | | |
|---|---|---|---|
| 2,035,386 | 3/1936 | Salzberg | 260/340.6 |
| 2,603,650 | 7/1952 | Schmerling | 260/345.1 |
| 3,931,238 | 1/1976 | Starks | 260/346.11 |
| 4,002,646 | 1/1977 | Robinson | 260/346.11 |
| 4,254,039 | 3/1981 | Murib et al. | 260/346.11 |
| 4,261,906 | 4/1981 | Renga et al. | 260/348.16 |
| 4,271,080 | 6/1981 | Murib | 260/346.11 |

FOREIGN PATENT DOCUMENTS

| | | | |
|---|---|---|---|
| 194850 | 5/1957 | Austria | 260/340.6 |
| 363895 | 12/1931 | United Kingdom | 260/340.6 |

OTHER PUBLICATIONS

Chem. Abstracts 65:5434f.
Chem. Abstracts 86:139904s.
Chem. Abstracts 50:8647e.
Grobelny et al. Tetrahedron Letters, No. 28, pp. 26, 39–42 (1979).
Chem. Berichte, 72B, pp. 2057–2062 (1939).

*Primary Examiner*—Ethel G. Love
*Attorney, Agent, or Firm*—Douglas N. Deline; David H. Thurston

[57] ABSTRACT

Cyclic ethers such as tetrahydrofuran, dioxane, and tetrahydropyran are produced by reacting dimethyl carbonate with an appropriate primary dihalide in the presence of a quaternary ammonium or phosphonium salt.

10 Claims, No Drawings

PREPARATION OF CYCLIC ETHERS

BACKGROUND OF THE INVENTION

This invention relates to a new chemical process for making cyclic ethers and diethers having five or six atoms in the ring structure. This new process is applicable to the preparation of cyclic ethers such as tetrahydrofuran, p-dioxane, tetrahydropyran, and phthalan.

In the past, such ethers have been made by dehydration of a corresponding diol, by dehydroacyloxylation of a monoester of the diol, or by the reaction of a dihalide or halo alcohol with a strong base. These known processes have a number of disadvantages including intricate process equipment with substantial recycle of reactants, the production of relatively large volumes of inorganic salt by-product, and separation of the cyclic ether product from an aqueous reaction mixture.

It has been shown that a vicinal epoxide is formed by the thermal decomposition of a β-haloalkyl alkyl carbonate in the presence of a quaternary ammonium or phosphonium salt, see Renga et al., "Process for Making Vicinal Epoxides", Ser. No. 095,002, filed Nov. 16, 1979, now U.S. Pat. No. 4,261,906. It is also known that a linear aromatic alkyl ether is produced by the reaction of an aromatic alkyl carbonate with an alkyl halide in the presence of the same kind of quaternary salt catalyst, see Renga, "Process for Making Aromatic Ethers", Ser. No. 187,688, filed Sept. 16, 1980.

SUMMARY OF THE INVENTION

It has now been found that a cyclic ether of the formula

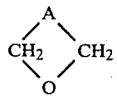

having five or six atoms in the ring structure is produced by contacting a lower alkyl carbonate $RR'CO_3$ with a primary dihalide of the formula $XCH_2\text{-}A\text{-}CH_2X$ at about 100° C. −200° C. in the presence of a small but catalytically effective amount of a quaternary ammonium or phosphonium salt. In the above formulas, R and R' each represent a methyl or ethyl radical, X represents either Br or Cl, and A is a divalent radical of the group 1,2- or 1,3-alkylene, 1,2-phenylene, oxydimethylene, and oxyethylene.

DETAILED DESCRIPTION OF THE INVENTION

In the reaction of the dihalide and the dialkyl carbonate defined above, the by-products are $CO_2$ and alkyl halide, both of which normally escape from the reaction mixture substantially as they are formed, thus separating themselves from the cyclic ether product and so driving the reaction to completion according to the equation:

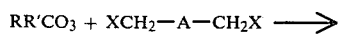

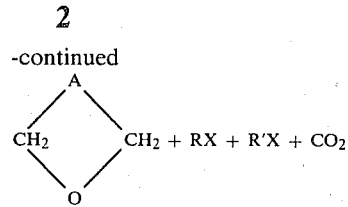

The alkyl halide by-product can be easily separated and recovered from the volatile effluent. Preferably, R and R' both represent a methyl group.

As defined above, the dihalide reactant can be a dichloride, a dibromide, or a bromochloride. For economic and other obvious reasons, the dihalide is preferably a dichloride. The A portion of the dihalide molecule can have one or more inert substituents such as lower alkyl or lower alkoxy groups. Thus, when A represents a 1,2- or 1,3-alkylene radical, not only the ethylene and trimethylene radicals are included, but also such substituted radicals as 1,2-propylene, 1-methoxy-1,3-propylene, 1,2-butylene, and the like. Similarly, the term phenylene in this case also includes methoxyphenylene, dimethylphenylene, and so on. Also, as herein defined, the term oxydimethylene includes the same radical having one or two lower alkyl substituents, and the term oxyethylene includes this radical having one or two lower alkyl or lower alkoxy substituents.

The proportion of dihalide and dialkyl carbonate reactants is not a critical factor. Preferably, the two reactants are employed in about equal molar quantities and, most preferably, with about 10–20 percent excess carbonate.

The reaction can be run effectively at any temperature within the defined range of about 100° C. −200° C., but for optimum results, a reaction temperature of about 120° C. −160° C. is preferred. Under these conditions, essential completion of the reaction is usually accomplished in about 10–100 hours.

For best results, this reaction is run using a polar solvent as reaction medium. Relatively high boiling inert solvents such as sulfolane, glycol diethers, and substituted aromatics such as anisole and o-dichlorobenzene are illustrative examples of solvents which may be used with added quaternary salt to catalyze the reaction.

Preferably, the solvent is an amide such as N,N-dimethylformamide or N,N-dimethylacetamide whereby the reaction is facilitated and catalyzed by small amounts of an ammonium halide salt formed in the reaction mixture from the amide solvent. No added quaternary salt catalyst is needed with such a solvent which serves as both a beneficial reaction medium and a source of reaction catalyst. Other nitrogen-containing solvents capable of forming a quaternary ammonium salt in significant quantity under reaction conditions are also operable, for example, alkylated pyridines.

The proportion of solvent in the reaction mixture is not critical, but optimum results and convenience in operating are found when the solvent constitutes about 50–80 percent of the total volume.

Substantially any quaternary ammonium or phosphonium salt can catalyze the reaction. Preferably, these salts have the general formula $(R'')_4AY$ where each $R''$ is a hydrocarbon moiety, A is a quaternary nitrogen or phosphorus atom, and Y is an inert (i.e., unreactive in this process) neutralizing anion which may be inorganic, e.g., chloride, bromide, iodide, bicarbonate, sulfate, or the like, or Y may be an organic ion such as formate, acetate, benzoate, phenate, or bisphenate. The R" groups may be alkyl, aryl, alkaryl, aralkyl, or cycloalkyl. Also, two R" groups may combine to form a heterocyclic ring. Illustrative quaternary salt catalysts are tetrabutylammonium iodide, benzyltriethylammonium chloride, N-methylpyridinium chloride, N,N-dibutylmorpholinium iodide, N-propylpyrrolium chloride, tetrabutylphosphonium bromide, tributylmethylphosphonium formate, tetrapropylphosphonium bisulfate, and similar ammonium and phosphonium salts with these and other such inorganic and organic neutralizing anions as described above. The catalytic salt may be added as such to the reaction mixture or it may be formed in situ.

Also, amine and phosphine salts such as tributylamine hydrochloride which are a form of quaternary salt will catalyze the reaction although these are generally less desirable in the reaction mixture.

Although any significant amount of such an added quaternary salt will catalyze the reaction to some extent, for practical reasons in batch operations, it is preferred to use about 0.1–10 mole percent of the salt based on the carbonate. More quaternary salt catalyst can be used but the excess confers little added advantage and may in fact be disadvantageous.

In a mode of the invention particularly adapted to continuous operation, one or more R groups may be pendant methylene groups from a resin matrix so that the quaternary salt is a salt form of a strong base anion-exchange resin such as DOWEX ® 21K, DOWEX ® 11, DOWEX ® MWA-1, or other such commercially available ion-exchange resins or the phosphonium equivalents of such quaternary ammonium-substituted resins. In such a continuous operation of the process, the mixed reactants are passed at an appropriate flow rate through a bed of the strong base anion resin maintained at a suitable temperature within the limits previously defined.

Batchwise operation of the process involves simply combining the reactants and catalyst and heating until the evolution of carbon dioxide and alkyl halide has ceased.

The process is ordinarily carried out at atmospheric pressure but it may be carried out at somewhat reduced pressure to hasten the removal by distillation of the volatile alkyl halide product. Passage of a stream of nitrogen or other inert gas through or over the reaction mixture may also be beneficial in this respect for some mixtures.

This process provides the advantages of a neutral reaction mixture, moderate temperature, and ready separation of the cyclic ether product as well as the alkyl halide coproduct. The volatile reaction products are carbon dioxide which can simply be vented and the alkyl halide which can be recovered by condensation or adsorption. The residue in the reaction vessel is primarily the desired ether together with the solvent and the small amount of quaternary salt catalyst and any excess of dialkyl carbonate reactant. The desired ether product is readily recovered and purified by conventional means such as distillation.

EXAMPLE 1

A mixture of 0.2 g mole of 1,4-dichlorobutane, 0.24 g mole of dimethyl carbonate, and 100 ml of N,N-dimethylformamide was heated in a reaction flask equipped with reflux condenser vented through a solid $CO_2$-+acetone-cooled trap. After heating in an oil bath with bath at 150° C. for 20 hours, $CO_2$ evolution from the reaction mixture had stopped and the internal temperature had dropped from 135° C. to 127° C. The cold trap was allowed to warm to room temperature and 1.76 g of tetrahydrofuran was found to be present. Distillation of the reaction mixture produced another 9.9 g of tetrahydrofuran for a total isolated yield of 81 percent based on the starting dichloride. Gas chromatographic analysis of the remaining reaction mixture indicated additional tetrahydrofuran for an overall total yield of 88 percent.

EXAMPLE 2

Example 1 was repeated using 100 ml of N,N-dimethylacetamide instead of the dimethylformamide. After 44 hours of heating, 10.3 g of tetrahydrofuran was isolated for an isolated yield of 78 percent. An overall total yield of 85 percent was found by gas chromatographic analysis of the remaining reaction mixture.

EXAMPLE 3

The procedure of Example 1 was followed using 0.1 g mole of 1,4-dibromobutane, 0.11 g mole of dimethyl carbonate, and 50 ml of N,N-dimethylformamide as the constituents of the reaction mixture. After heating for 24 hours on a 150° C. oil bath, a total of 3.2 g (44 percent yield) of tetrahydrofuran was isolated as before.

EXAMPLE 4

The procedure of Example 1 was followed using a reaction mixture of 0.2 g mole of bis(2-chloroethyl) ether, 0.24 g mole of dimethyl carbonate, and 100 ml of N,N-dimethylformamide. After 24 hours on a 150° C. oil bath, 13.3 g of p-dioxane was isolated as above for a yield of 75 percent. A total yield of 84 percent was estimated by analysis of the reaction mixture.

EXAMPLE 5

The procedure described in Example 1 was followed in reacting 0.05 g mole of $\alpha,\alpha'$-dichloro-o-xylene with 0.06 g mole of dimethyl carbonate in 50 ml of N,N-dimethylformamide. After 22 hours, the reaction mixture was poured into 100 ml of water and the organic portion was extracted from the mixture with three 50-ml portions of hexane. The combined extracts were dried over $MgSO_4$ and the hexane was distilled off. The residue was distilled under reduced pressure to obtain 2.29 g (37 percent yield) of phthalan (1,3-dihydroisobenzofuran), b.p. 95° C./30 mm.

EXAMPLE 6

Similarly, a mixture of 0.2 g mole of 1,5-dichloropentane and 0.24 g mole of dimethyl carbonate in 100 ml of DMF was reacted for 22 hours at the same temperature and the reaction mixture was worked up in the same way to obtain 2.84 g (17 percent yield) of distilled tetrahydropyran.

Using the reaction procedure described above, dimethyl carbonate is reacted with bis(1-chloro-2-propyl) ether to produce 2,6-dimethyl-p-dioxane, with 1,4-dichloro-2-methylbutane to make 3-methyltetrahydrofuran, with 1,4-dichloro-2,3-dimethylbutane to make 3,4-dimethyltetrahydrofuran, and with chloromethyl 2-chloroethyl ether to produce 1,3-dioxolane.

I claim:

1. A process for making a cyclic ether of the formula

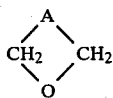

having five to six atoms in the cyclic ether ring structure, which process comprises contacting a lower alkyl carbonate of the formula RR′CO$_3$ wherein R and R′ are each independently a methyl or ethyl radical with a dihalide of the formula XCH$_2$-A-CH$_2$X wherein each X is Cl or Br and A is a divalent radical of the group 1,2-alkylene, 1,3-alkylene, 1,2-phenylene, oxydimethylene and oxyethylene in the presence of a quaternary ammonium or phosphonium salt at about 100° C. −200° C.

2. The process of claim 1 wherein R and R′ are both methyl radicals.

3. The process of claim 2 wherein X represents Cl.

4. The process of claim 3 wherein the reaction is carried out in a polar solvent medium.

5. The process of claim 4 wherein the solvent is N,N-dimethylformamide or N,N-dimethylacetamide.

6. The process of claim 5 wherein the dihalide reactant is 1,4-dichlorobutane and the cyclic ether product is tetrahydrofuran.

7. The process of claim 5 wherein the dihalide reactant is bis(2-chloroethyl) ether and the cyclic ether product is p-dioxane.

8. The process of claim 5 wherein the dihalide reactant is α,α′-dichloro-o-xylene and the cyclic ether product is phthalan.

9. The process of claim 5 wherein the dihalide reactant is 1,5-dichloropentane and the cyclic ether product is tetrahydropyran.

10. The process of claim 1 wherein the temperature is about 120° C. −160° C.

* * * * *